US008925821B2

United States Patent
Berssen et al.

(10) Patent No.: US 8,925,821 B2
(45) Date of Patent: Jan. 6, 2015

(54) METHOD FOR LOCATING AN OPTICAL IDENTIFICATION ON A LABORATORY ANALYSIS CUVETTE

(75) Inventors: Johannes Berssen, Panketal (DE); Clemens Hanschke, Berlin (DE)

(73) Assignee: Hach Lange GmbH, Berlin (DE)

( * ) Notice: Subject to any disclaimer, the term of this patent is extended or adjusted under 35 U.S.C. 154(b) by 0 days.

(21) Appl. No.: 13/988,762

(22) PCT Filed: Nov. 16, 2011

(86) PCT No.: PCT/EP2011/070236
§ 371 (c)(1),
(2), (4) Date: Jul. 22, 2013

(87) PCT Pub. No.: WO2012/069345
PCT Pub. Date: May 31, 2012

(65) Prior Publication Data
US 2013/0306732 A1    Nov. 21, 2013

(30) Foreign Application Priority Data
Nov. 23, 2010  (EP) .................................... 10192199

(51) Int. Cl.
*G06K 5/04*  (2006.01)
*G01N 35/00*  (2006.01)
*G06K 7/10*  (2006.01)
*B01L 3/00*  (2006.01)

(52) U.S. Cl.
CPC ...... *G01N 35/00732* (2013.01); *G06K 7/10792* (2013.01); *G06K 7/10722* (2013.01); *G06K 7/10861* (2013.01); *B01L 3/5453* (2013.01); *G01N 2035/00752* (2013.01); *G01N 2035/00772* (2013.01); *B01L 2200/025* (2013.01); *B01L 2200/143* (2013.01); *B01L 2300/021* (2013.01)
USPC ..................................... 235/462.08; 235/454

(58) Field of Classification Search
CPC ... G06K 7/14; G06K 7/10851; G06K 7/1443; G06K 7/1093; B01L 3/5453; G01N 35/00732; G01N 21/78
USPC ........................... 235/462.08, 454; 422/82.05
See application file for complete search history.

(56) References Cited

U.S. PATENT DOCUMENTS

| 4,595,562 A | 6/1986 | Liston et al. |
| 5,386,287 A | 1/1995 | Berssen et al. |
| 5,455,006 A | 10/1995 | Aota et al. |
| 2005/0196323 A1 | 9/2005 | Itoh |

FOREIGN PATENT DOCUMENTS

| CN | 1111353 A | 11/1995 |
| CN | 1667419 A | 9/2005 |
| DE | 27 33 074 A1 | 2/1979 |
| DE | 41 09 118 A1 | 9/1992 |
| DE | 41 09 118 C2 | 4/1995 |

*Primary Examiner* — Sonji Johnson
(74) *Attorney, Agent, or Firm* — Norman B. Thot

(57) ABSTRACT

A method for locating an optical identification on a cuvette includes providing a cuvette comprising an axial locating bar with a fixed bar width with a fixed geometric relationship with an identification. A laboratory analyzer is provided comprising a cuvette chamber, a cuvette rotating device, and a digital camera with an axial resolution of more than 10 lines. The digital camera is associated with the cuvette chamber. At least four respective non-adjacent lines of the digital camera are read in. The identification is searched for. If at least three mutually successive read-in lines comprising approximately axially in-line reflection signals of the axial locating bar with the fixed bar width are registered, the cuvette is rotated by an angle corresponding to the fixed geometric relationship so that identification is aligned with the digital camera. The identification is read in by reading out a plurality of adjacent lines of the digital camera.

11 Claims, 3 Drawing Sheets

METHOD FOR LOCATING AN OPTICAL IDENTIFICATION ON A LABORATORY ANALYSIS CUVETTE

CROSS REFERENCE TO PRIOR APPLICATIONS

This application is a U.S. National Phase application under 35 U.S.C. §371 of International Application No. PCT/EP2011/070236, filed on Nov. 16, 2011 and which claims benefit to European Patent Application No. 10192199.7, filed on Nov. 23, 2010. The International Application was published in German on May 31, 2012 as WO 2012/069345 A1 under PCT Article 21(2).

FIELD

The present invention relates to a method for locating an optical identification on a laboratory analysis cuvette in a laboratory analyzer, and to a laboratory analysis measuring device for performing the method.

BACKGROUND

DE 41 09 118 C2 describes a method for an automatic evaluation of a substance contained in a water sample, wherein a laboratory analysis cuvette comprises an optical identification in the form of a barcode. The associated laboratory analyzer comprises a cuvette chamber with a cuvette rotating device. A reading device is further provided in the cuvette chamber, by means of which the cuvette barcode can be read out, while the cuvette is rotated in the cuvette chamber by the cuvette rotating device. The reading device scans in a punctiform manner. Locating the barcode takes relatively long in adverse conditions since the start of the barcode first needs to be located.

SUMMARY

An aspect of the present invention to provide a method for more rapidly locating an optical identification on a laboratory analysis cuvette in a laboratory analyzer, and to provide a laboratory analysis measuring arrangement for performing the method.

In an embodiment, the present invention provides a method for locating an optical identification on a cylindrical laboratory analysis cuvette which includes providing a cuvette configured to be cylindrical and to contain a reagent. The cuvette comprises an axial locating bar with a fixed bar width, and at least one identification. The axial locating bar is configured so as to be in a fixed geometric relationship with the at least one identification. A laboratory analyzer is provided comprising a vertical cuvette chamber, a cuvette rotating device, and a digital camera with an axial resolution of more than 10 lines. The digital camera is configured to be associated with the vertical cuvette chamber. At least four respective non-adjacent lines of the digital camera are read in. The at least one identification is searched for, and, if at least three mutually successive read-in lines comprising approximately axially in-line reflection signals of the axial locating bar with the fixed bar width are registered, the cuvette is rotated by an angle corresponding to the fixed geometric relationship so that the at least one identification is aligned with the digital camera.

BRIEF DESCRIPTION OF THE DRAWINGS

The present invention is described in greater detail below on the basis of embodiments and of the drawings in which.

DETAILED DESCRIPTION

Figure 1:
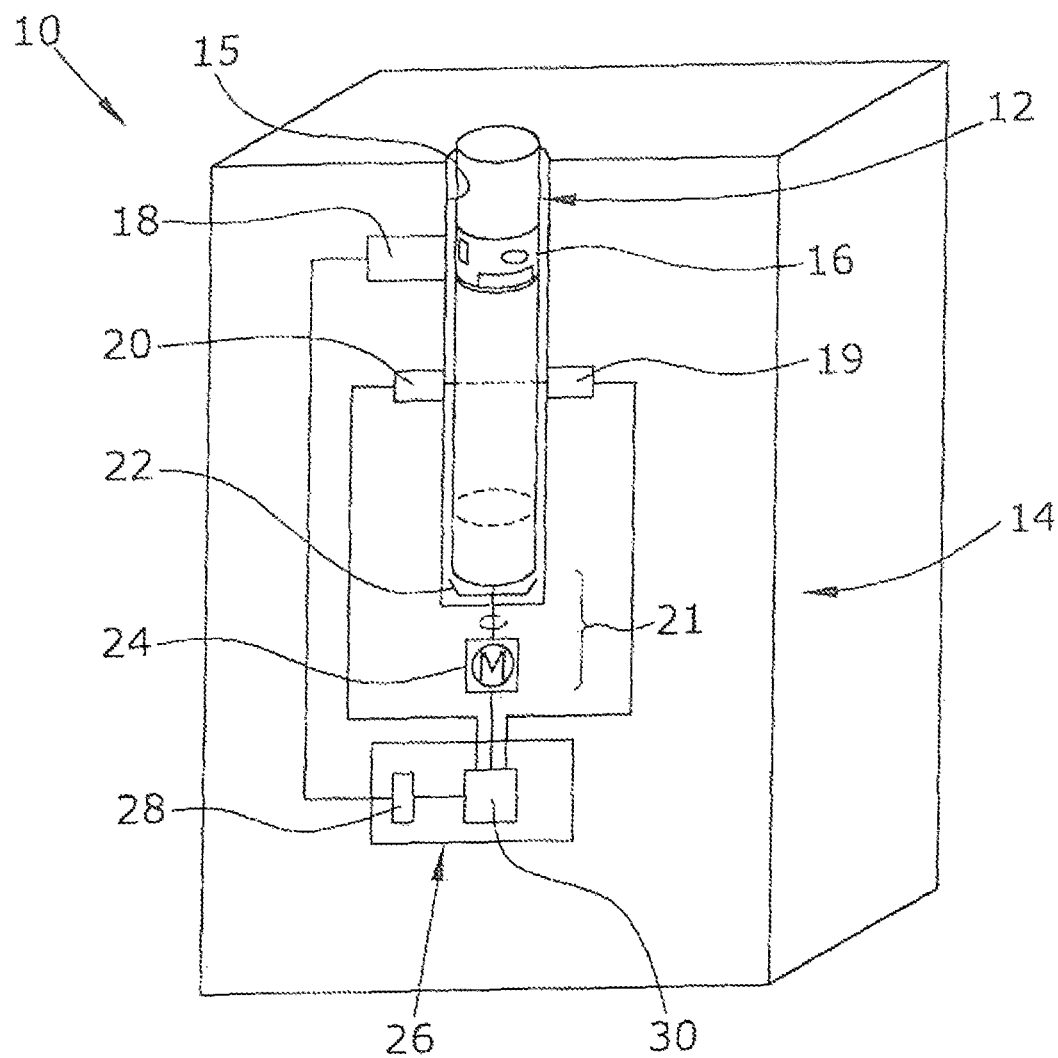
FIG. 1 shows a schematic illustration of a laboratory analyzer measuring arrangement with a laboratory analyzer and a laboratory analyzer cuvette.

The method of the present invention and the device of the present invention are directed, respectively, to locating an optical identification on a cylindrical laboratory analyzer cuvette containing a reagent and to a laboratory analysis measuring device formed by a laboratory analyzer and a laboratory analyzer cuvette for performing the above-described method.

The laboratory analyzer comprises a vertical cuvette chamber into which the cuvette is inserted for performing a quantitative determination of an analyte in a water sample.

The cuvette comprises at least one optical identification, for example, a graphical identification of origin or a one- or two-dimensional barcode. The identification contains information about the type and/or the origin of the cuvette. The identification is suited for being read by a digital camera. For this purpose, the identification should be represented with contrasts which are as rich as possible. The cuvette further has an axial locating bar with a constant bar width. The locating bar may be a white strip on a black background. The term "axial", as used herein, always means vertical since the cuvette can be placed into the correspondingly vertically oriented cuvette chamber exclusively in vertical orientation.

The laboratory analyzer comprises a digital camera at the cuvette chamber which has an axial resolution (i.e., vertical resolution) of more than 10 lines. The digital camera can be an axially-oriented (i.e., vertically-oriented) line scan camera, but it may also be an area scan camera capable of taking a two-dimensional image. If the digital camera is designed as a line scan camera, a resolution of more than 10 lines means the number of pixels arranged one above the other in the vertical direction which can record a corresponding number of lines as the cuvette is rotated by the cuvette rotating device.

If the digital camera is designed as an area scan camera, a circular section of the cuvette can basically also be read in when the cuvette is standing still, with a plurality of circular sections of the cuvette being scanned one after the other intermittently in order to thereby scan the entire circumference of the cuvette. This procedure is in particular advantageous when reading in the optical identification.

According to the method, first, at least four lines of the digital camera that are not adjacent to each other are read in. If the digital camera is designed as a (vertical) line scan camera, the cuvette is rotated at a constant rotation speed by the cuvette rotation device during the reading operation. If the digital camera is designed as an area scan camera, a single vertical column of the digital camera can be activated in these method steps, while all other columns are inactive, so that the area scan camera is used only as a vertical line camera. As an alternative, provided the camera is an area scan camera, it is also possible in this method step to take a plurality of pictures of the cuvette in an intermittent manner so that the entire circumference of the cuvette is thus scanned.

When reading in, at most every second line of the digital camera is read in, for example, at most every fourth line, and, for example, at most every eighth line. In this manner the data volume to be evaluated is drastically reduced and the locating bar can quickly be located.

Only when at least three, for example, at least four mutually successive read-in lines determine approximately in-line reflection signals with the correct bar width, reflected by the locating bar, is it assumed that the locating bar has been located. As long as less than three, for example, less than four mutually successive read-in lines determine approximately in-line reflection signals with the correct bar width, reflected by the locating bar, the cuvette is rotated on and the search for the locating bar is continued. In this method step, successive read-in lines are the successive active lines, i.e., only those lines that are active in this method step. One or a plurality of non-active lines can thus exist between two successive active lines.

The locating bar is in a fixed geometric relationship with the identification or the identifications on the cuvette. The geometric relationship can be expressed, for example, by a rotation angle α, β and, as the case may be, by a vertical vector.

After the locating bar has been located, the cuvette is rotated by the rotation angle α, β corresponding to the geometric relationship, such that the identification or one of the identifications is aligned with the digital camera such that the identification can be detected quickly by the digital camera in this position.

For the purpose of controlling the method, the laboratory analyzer is provided with a control including an identification search module.

The above-described method and the above-described device significantly accelerate the search for the optical identification since the data volume to be evaluated in this process is greatly reduced, in particular in the case of a digital camera designed as an area scan camera.

The following is a detailed description of an embodiment of the present invention with reference to the drawings.

FIG. 1 schematically illustrates a laboratory analysis measuring arrangement 10 formed by a laboratory analyzer 14 and a laboratory analyzer cuvette 12. The measuring arrangement 10 serves to determine a certain analyte in a water sample. For this purpose, the cuvette 12 contains a dried solid reagent 34 which reacts in a color-modifying manner with the relevant analyte in the water sample pipetted into the cuvette 12. In the laboratory analyzer 14, the concentration of the analyte in the water sample is determined in a transmissive manner by means of a photometer 19, 20 which is formed essentially by a transmitter 19 and a receiver 20.

The laboratory analyzer 14 has a digital camera 18, designed as an area scan camera, which is arranged on the cylindrical side wall of a vertical cuvette chamber 15. The digital camera 18 may alternatively be operated in an area scan mode or a column scan mode, as will be explained below.

The cuvette chamber 15 is associated with a cuvette rotation device 21 formed by a rotary plate 22 in the region of the cuvette chamber 15 and by an electric drive motor 24 rotating the rotary plate 22, if needed.

The laboratory analyzer 14 further comprises a digital apparatus control 26 with an identification search module 28 and a central unit 30. The identification search module 28 controls the quick locating and reading of an identification 54, 56 on a label 16 of the cuvette 12.

Figure 2:
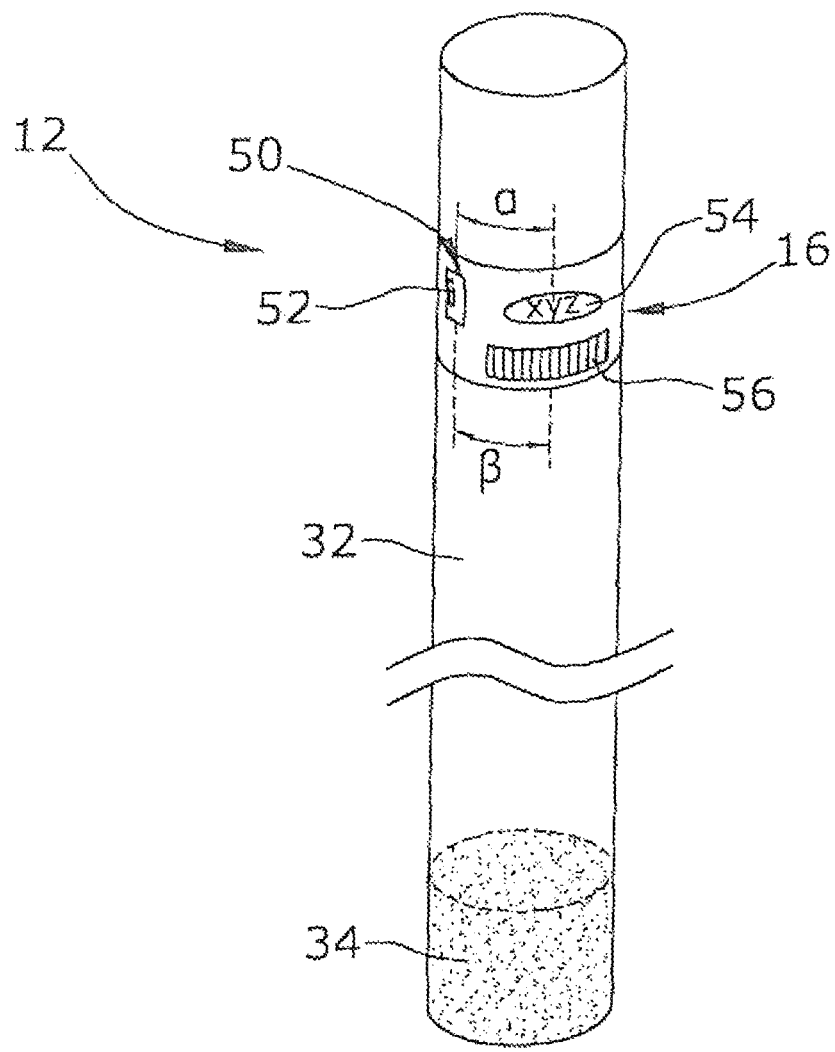
FIG. 2 shows an upscale illustration of the laboratory analyzer cuvette of FIG. 1 including a label with two identifications and a locating bar.

The cuvette 12, illustrated in detail in FIG. 2, is essentially formed by a transparent cylindrical cuvette body 32 of glass, whose bottom is closed. In the bottom portion of the cuvette body 32, the reagent 34 is stored in solid, dried form.

A water-resistant paper or plastics label 16 is stuck on the cuvette body 32, which label 16 is printed in black and white with an axial locating bar 50, a first identification 54 and a second identification 56. The locating bar 50 is designed as a white vertical strip 52 of constant horizontal width B on a black background. The first identification 54 is arranged on the label 16 at the same height as the locating bar 50, and can be formed, for instance, by the company name or the so-called logo of the manufacturer of the cuvette 12 or of the laboratory analyzer 14. The second identification 56 can be a one-dimensional or a two-dimensional barcode which, in encoded form, includes information about the manufacturer, the batch, the shelf-life, the reagent or the analyte to be analyzed.

Both identifications 54, 56 are in a fixed and always constant geometric relationship with the locating bar 50. The first identification 54 is at approximately the same vertical height as the locating bar 50 and its central axis of symmetry is offset from the locating bar 50 by a rotation angle α. The second identification 56 is arranged offset both axially and, with respect to its axis of symmetry, rotationally from the locating bar 50 by an angle β. The geometric relationship is always the same for all cuvettes 12, irrespective of the type of reagent 32 they contain or of the analyte they are provided for.

Figure 3:
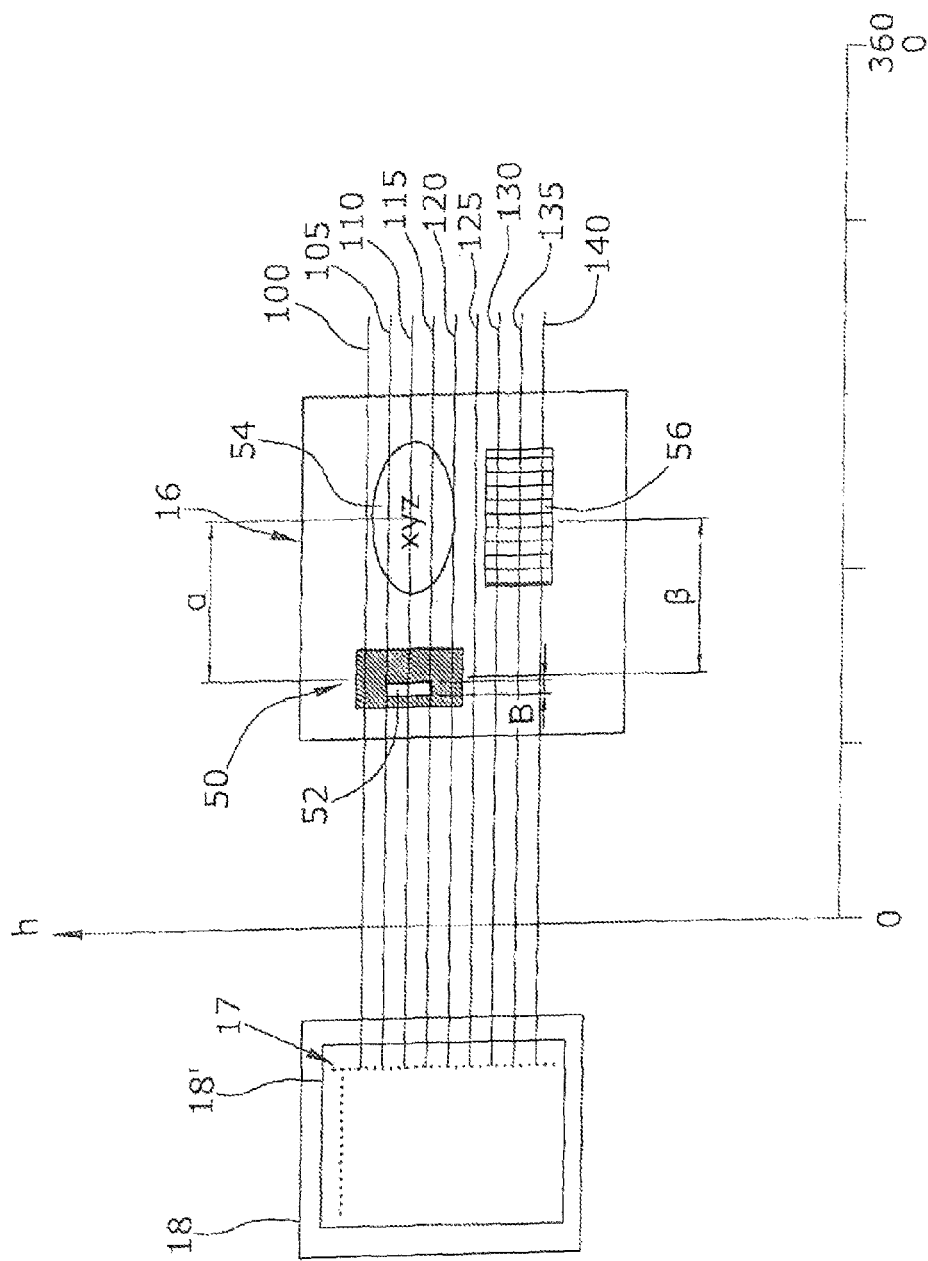
FIG. 3 shows a flat projection of the label in FIG. 2.

FIG. 3 schematically shows a flat projection of the label 16 of a cuvette 12 placed in the cuvette chamber 15 and the digital camera 18. The digital camera 18, designed as an area scan camera, has a CCD chip 18' having a resolution of, for example, 320×320 pixels, i.e. 320 lines and 320 columns.

For searching the locating bar 50, only a single column 17 of the CCD chip 18' is activated. In this single column 17, only nine non-adjacent lines 100, 105, 110, 115, 120, 125, 130, 135, 140 are activated or read out by the identification search module 28, these lines being separated respectively by thirty-eight non-active lines.

For searching the locating bar 50, the cuvette rotating device 21, controlled by the central control unit 30, rotates the cuvette 12, filled with a water sample and placed in the cuvette chamber 15, at a constant rotation speed in the cuvette chamber 15, while, at the same time, the nine lines 100, 105, 110, 115, 120, 125, 130, 135, 140 of the digital camera 18 are read and evaluated by the identification search module 28. As soon as approximately axially in-line reflection signals with the bar width B, reflected from the locating bar 50, are detected for four mutually successive active read-in lines 105, 110, 115, 120, it is assumed that the locating bar 50 or the locating bar strip 52 has been located. This is reported to the central control unit 30 by the identification search module 28.

The cuvette 12 is then rotated by the cuvette rotating device 21 about the associated angle α of the first identification 54 to be read in thereafter, so as to align the first identification 54 with the digital camera 18 for the first identification 54 to be read. In the example illustrated in FIG. 3, the associated angle α indicates the rotational distance to the central symmetry axis of the first identification 54. As an alternative, the associated angle α may also indicate the rotational distance to the left or the right end of the respective identification, especially if the digital camera is a line scan camera.

In the present embodiment, after the central symmetry axis of the first identification 54 is aligned centrally with the digital camera 18, the digital camera reads in a two-dimensional full-surface picture of the first identification 54 and is checked for authenticity by the identification search module 28 or the central control unit 30. Thereafter or simultaneously, the second identification 56 in the form of a two-dimensional barcode can be read in and be decoded correspondingly.

Finally, based on the information acquired from the second identification 56, the water sample in the cuvette 12 is analyzed by photometry using the photometer 19, 20.

The present invention is not limited to embodiments described herein; reference should be had to the appended claims.

What is claimed is:

1. A method for locating an optical identification on a cylindrical laboratory analysis cuvette, the method comprising:
   providing a cuvette configured to be cylindrical and to contain a reagent, the cuvette comprising an axial locating bar with a fixed bar width, and at least one identification, the axial locating bar being configured so as to be in a fixed geometric relationship with the at least one identification;
   providing a laboratory analyzer comprising a vertical cuvette chamber, a cuvette rotating device, and a digital camera with an axial resolution of more than 10 lines, the digital camera being configured to be associated with the vertical cuvette chamber;
   reading in at least four respective non-adjacent lines of the digital camera;
   searching for the at least one identification, and, if at least three mutually successive read-in lines comprising approximately axially in-line reflection signals of the axial locating bar with the fixed bar width are registered;
   rotating the cuvette by an angle corresponding to the fixed geometric relationship so that the at least one identification is aligned with the digital camera; and
   reading in the at least one identification by reading out a plurality of adjacent lines of the digital camera.

2. The method as recited in claim 1, wherein at least six non-adjacent lines of the digital camera are read in, and further comprising:
   determining a rotational position of the locating bar so that at least four mutually successive read-in lines comprising approximately axially in-line reflection signals of axial locating bar with the fixed bar width are registered.

3. The method as recited in claim 1, wherein the digital camera is an area scan camera, and wherein the reading is performed when the cuvette rotating device is stationary.

4. The method as recited in claim 1, wherein the axial locating bar is provided as a white vertical strip on a black background.

5. The method as recited in claim 1, wherein the at least one identification is a barcode.

6. The method as recited in claim 1, wherein the at least one identification is a graphical identification of origin.

7. A laboratory analysis measuring arrangement comprising:
   a cuvette configured to be cylindrical and to contain a reagent, the cuvette comprising an axial locating bar with a fixed bar width, and at least one identification, the axial locating bar being configured so as to be in a fixed geometric relationship with the at least one identification, the reagent being configured to provide a quantitative determination of an analyte in water;
   a laboratory analyzer comprising a cuvette chamber configured to receive the cuvette, a cuvette rotating device arranged in the cuvette chamber, and a digital camera with an axial resolution of more than 10 lines, the digital camera being configured to be associated with the cuvette chamber; and
   a control comprising an identification search module which, via the cuvette rotating device, is configured to rotate the cuvette about an angle corresponding to the fixed geometric relationship so that the at least one identification is aligned with the digital camera if at least three mutually successive read-in lines register approximately axially in-line reflection signals of the locating bar with the fixed bar width.

8. The laboratory analysis measuring arrangement as recited in claim 7, wherein the digital camera is an area scan camera, and a reading is performed when the cuvette rotating device is stationary.

9. The laboratory analysis measuring arrangement as recited in claim 7, wherein the locating bar is provided as a white vertical strip on a black background.

10. The laboratory analysis measuring arrangement as recited in claim 7, wherein the at least one identification is a barcode.

11. The laboratory analysis measuring arrangement as recited in claim 7, wherein the at least one identification is a graphical identification of origin.

* * * * *